United States Patent
Corneliusson

(10) Patent No.: US 7,578,811 B2
(45) Date of Patent: Aug. 25, 2009

(54) ABSORBENT ARTICLE HAVING DISCRETE TAPERED FASTENING ELEMENTS

(75) Inventor: Helena Corneliusson, Bohus (SE)

(73) Assignee: SCA Hygiene Products AB, Gothenburg (SE)

( * ) Notice: Subject to any disclaimer, the term of this patent is extended or adjusted under 35 U.S.C. 154(b) by 262 days.

(21) Appl. No.: 10/610,653

(22) Filed: Jul. 2, 2003

(65) Prior Publication Data

US 2004/0044325 A1     Mar. 4, 2004

Related U.S. Application Data

(60) Provisional application No. 60/393,107, filed on Jul. 3, 2002.

(51) Int. Cl.
    *A61F 13/15*     (2006.01)
(52) U.S. Cl. .................. 604/389; 604/391; 604/385.01
(58) Field of Classification Search ......... 604/389–392, 604/385.01, 386, 355, 358, 393; 24/491; D24/125–126; 156/73.1, 63, 264
    See application file for complete search history.

(56) References Cited

U.S. PATENT DOCUMENTS

| | | | | | |
|---|---|---|---|---|---|
| 1,356,937 | A | * | 10/1920 | Miyamoto | 604/397 |
| 1,836,794 | A | * | 12/1931 | Goldstein | 604/392 |
| 2,122,417 | A | * | 7/1938 | Fridolph | 604/386 |
| 2,664,895 | A | * | 1/1954 | Shulman | 604/366 |
| 2,834,347 | A | * | 5/1958 | Connally | 604/389 |
| 3,205,549 | A | * | 9/1965 | Keech | 24/571 |
| 3,559,648 | A | * | 2/1971 | Mason, Jr. | 604/375 |
| 4,585,450 | A | * | 4/1986 | Rosch et al. | 604/390 |
| 4,850,992 | A | * | 7/1989 | Amaral et al. | 604/389 |
| D342,786 | S | * | 12/1993 | De Gooijer | D24/126 |
| 5,312,387 | A | * | 5/1994 | Rossini et al. | 604/389 |
| 5,342,344 | A | * | 8/1994 | Lancaster et al. | 604/387 |
| 6,174,303 | B1 | * | 1/2001 | Suprise et al. | 604/385.29 |
| 6,200,299 | B1 | * | 3/2001 | Heki | 604/386 |
| 6,976,978 | B2 | * | 12/2005 | Ruman et al. | 604/385.01 |
| 2004/0044324 | A1 | * | 3/2004 | Swenson et al. | 604/386 |

FOREIGN PATENT DOCUMENTS

| | | | |
|---|---|---|---|
| EP | 1350494 A1 | * | 10/2003 |
| GB | 2185383 A | * | 7/1987 |

* cited by examiner

*Primary Examiner*—Tatyana Zalukaeva
*Assistant Examiner*—Lynne Anderson
(74) *Attorney, Agent, or Firm*—Buchanan Ingersoll & Rooney PC

(57) ABSTRACT

A method for cutting discrete fastening elements (15A-15D) out of a web (15) of fastening element material and attaching the cut-out fastening elements to a web (3) of surface layer material. The method includes the following steps: sequences of four trapezoid fastening elements (15A-15D) are cut out of a web (15) of fastening element material, after which the first and fourth fastening elements on the one hand and the second and third fastening elements on the other hand are attached to a web (3) of surface layer material so that the first (15A) and fourth (15D) fastening elements on the one hand and the second (15B) and third (15C) fastening elements on the other hand are attached to successive absorbent articles in the process line. An absorbent article provided with such fastening elements is also disclosed.

11 Claims, 3 Drawing Sheets

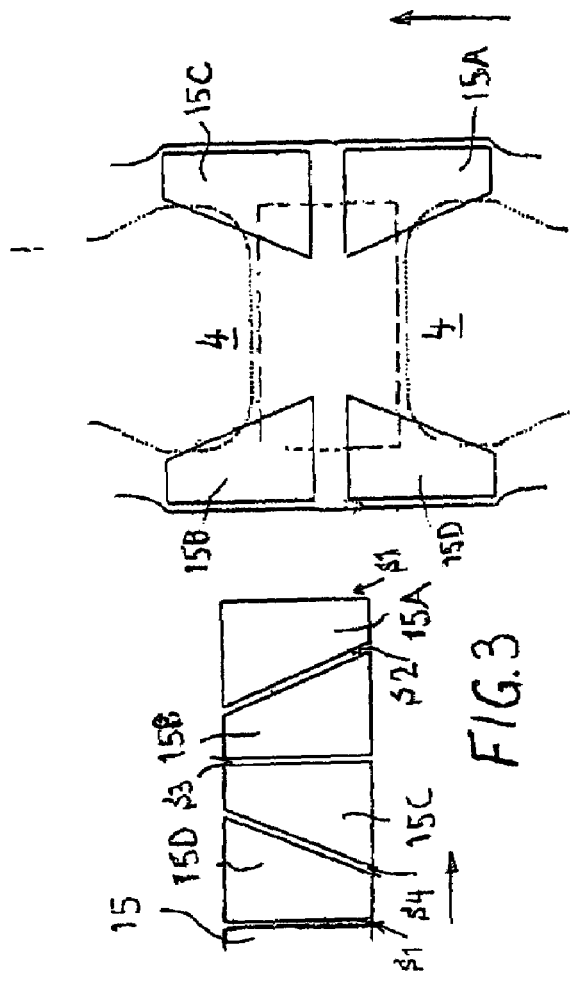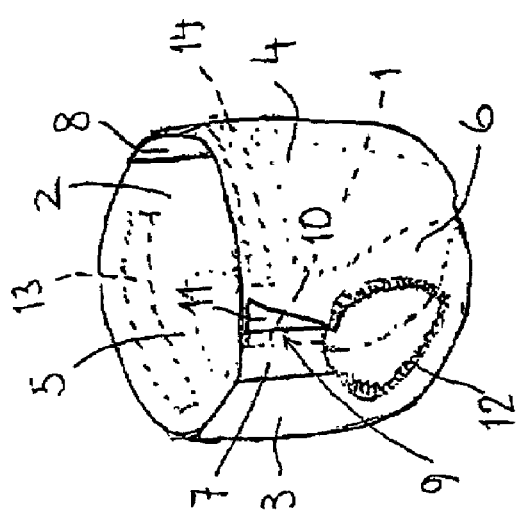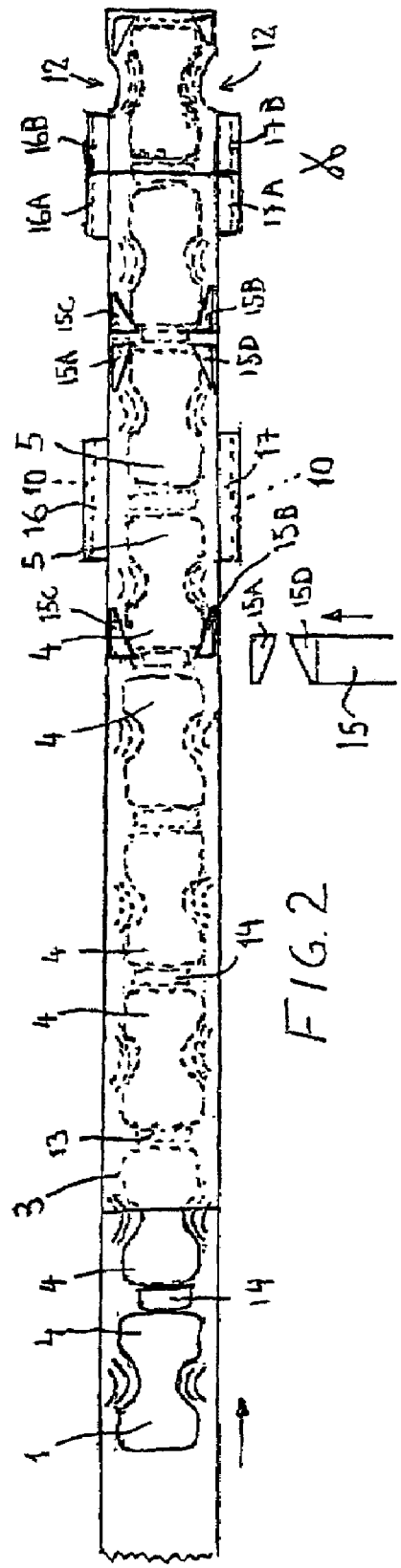

ABSORBENT ARTICLE HAVING DISCRETE TAPERED FASTENING ELEMENTS

CROSS-REFERENCE TO RELATED APPLICATIONS

The present application claims the benefit of U.S. Provisional Application No. 60/393,107, filed in the United States on Jul. 3, 2002, the entire contents of which are hereby incorporated herein by reference.

BACKGROUND OF THE APPLICATION

1. Technical Field

The present invention relates to a method for cutting discrete fastening elements out of a web of fastening element material and attaching the cut-out fastening elements to a web of surface layer material forming part of a process line for manufacturing absorbent articles, such as diapers, pant diapers or incontinence pads, and also to an absorbent article provided with such fastening elements.

2. Background Art

It has to be possible for diapers, pant diapers, incontinence pads and similar disposable articles to fit different sizes and shapes of wearer in order for a reasonable number of sizes of article to be sufficient for the requirements of the wearers. Traditionally, it has been possible for the size of the waist of diapers to be adjusted by virtue of the possibility of the side portions of the diaper overlapping one another to a varying degree. To this end, the diaper comprises fastening tapes which can be fastened in different places along the circumference of the waist, either directly to the surface layer material of the diaper or to a strip made of a material which allows the fastening tape to be fastened a number of times. Another possibility used for adapting an article according to the above to several sizes and for improving the fit of the article is to make the waistband either completely or partly elastic. Many modern absorbent articles according to the above make use of both these possibilities and therefore have both adjustable fastening elements and waist elastic. Furthermore, openable and reclosable pant diapers are known, in which the fastening elements are designed in such a manner that the side portions are fastened to one another along their entire length. The fastening elements consist of male and female elements of hook and loop means or tape/plastic strip. The female elements constitute receiving elements, and their extent in the circumferential direction determines the adjustment length.

The materials used for fastening elements are often considerably more expensive than other materials included in an absorbent article, and the cost of the fastening elements therefore constitutes a not inconsiderable proportion of the overall cost of the article. Moreover, the presence of the fastening elements also influences the characteristics of the product, such as rigidity, breathability, flexibility. It is therefore an advantage to use as little fastening element material as possible in the manufacture of absorbent articles.

OBJECTS AND SUMMARY

It is an object of the invention to provide a method in which fastening elements can be cut out and applied to an absorbent article without waste of fastening element material. It is also an object of the invention to produce fastening elements which allow a certain adjustment length of the waistband with a lower consumption of fastening element material than in previously known absorbent articles.

These objects are achieved by a method for cutting discrete fastening elements out of a web of fastening element material and attaching the cut-out fastening elements to a web of surface layer material forming part of a process line for manufacturing absorbent articles, such as diapers, pant diapers or incontinence pads, in which the individual articles in the process line have their front edges facing one another. The method comprises cutting out of a web of fastening element material sequences of four fastening elements, which fastening elements each have mutually opposite short sides and long sides, and the sequence is arranged such that the longest short sides of the first and fourth fastening elements extend along a same line as the shortest short sides and wherein the longest short sides of the second and third fastening elements extend along a same line as the shortest short sides of the first and fourth fastening elements; in addition to which the shortest long side of each fastening element is at right angles to the short sides, after which cutting out, the first and fourth fastening elements and the second and third fastening elements are attached to the web of surface layer material with the short sides extending along a same transverse line of the web of surface layer material, with the shortest long sides located next to the side edges of the web of surface layer material and extending in its longitudinal direction and with the longest short sides of the first and fourth fastening elements facing the longest short sides of the second and third fastening elements so that the first and fourth fastening elements on the one hand and the second and third fastening elements on the other hand are attached to successive absorbent articles in the process line.

In such an embodiment, the waist size can be reduced to an extent which is determined by the length of the long short sides of the fastening elements by virtue of a second fastening element which interacts with the fastening elements being fastened obliquely on the fastening elements. At the same time, the size of the leg openings can be reduced to an extent which is determined by the length of the short sides. Furthermore, no waste of fastening element material occurs in manufacture, and, after cutting-out, the fastening elements have their long short sides facing in the correct direction and can be applied to the articles without having to be rotated.

In a preferred embodiment, the material in the web of surface layer material consists of a liquidtight plastic material. Alternatively, the material in the web of surface layer material can consist of a liquid-permeable material.

The fastening elements are preferably attached to the surface layer material by means of thermal or ultrasonic welding, but gluing can also be used.

The fastening elements preferably comprise loop means designed to interact with hook means of a second fastening element which interacts with the fastening elements, but the fastening elements can also be made of plastic material in order to interact with second fastening elements of adhesive type.

The invention also relates to an absorbent article, such as a diaper, a pant diaper or an incontinence pad, comprising an absorption body enclosed between an inner liquid-permeable surface layer and an outer liquidtight surface layer and also a front portion, a rear portion and a crotch portion which lies between these portions and includes and is delimited by the leg openings of the article, and also fastening means for openably and reclosably fastening mutually opposite side parts of the front portion and the rear portion to one another, which fastening means consist of interacting pairs of fastening elements, which extend along the side edges of the front and rear portions, characterized in that one of the elements in the pairs of fastening elements tapers continuously from the end of the front portion or rear portion towards the leg opening.

BRIEF DESCRIPTION OF THE DRAWINGS

The invention will now be described with reference to accompanying figures, in which:

FIG. 1 shows diagrammatically a perspective view of a diaper according to an embodiment of the invention, FIG. 2 illustrates diagrammatically the various steps in the manufacture of the diaper in FIG. 1, FIG. 3 shows a portion of FIG. 2 on larger scale.

DETAILED DESCRIPTION OF THE PREFERRED EMBODIMENTS

Figure 5:
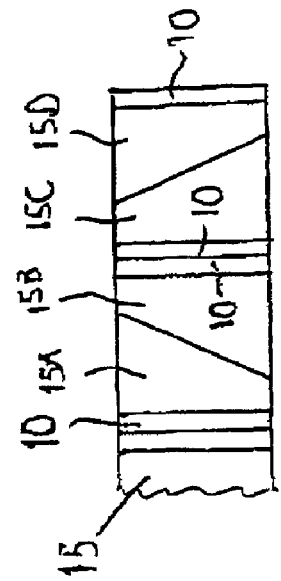
FIG. 5 shows diagrammatically a fastening means web which can be used in the manufacture of diaper pants according to an embodiment of the invention.

FIG. 1 shows a diaper according to a preferred embodiment of the invention. The pant diaper shown in FIG. 1 comprises an absorption body 1 enclosed between an inner surface layer 2 made of liquid-permeable material and an outer surface layer 3 made of liquidtight material. The surface layers 2 and 3 are interconnected by gluing or welding in parts lying outside the absorption body. The unit formed by the surface layers and the absorption body has a front portion 4, a rear portion 5 and an intermediate narrower crotch portion 6 which is delimited by the leg openings of the diaper. The diaper also comprises side panels 7, 8 which are attached to the side edges of the rear portion.

The side panels 7, 8 bear one fastening element of a reclosable fastening means 9 which connects the side edges of the panels 7, 8 to the front portion 4, and the second fastening element is attached to the front portion 4 of the diaper. In the example shown, the fastening means 9 is of the hook and loop type, that is to say one fastening element 10, the male element, is provided with a large number of hooks which project from the surface of the fastening element, and the other fastening element 11, the female element, is provided with a large number of loops into which the hooks fit. The fastening means 9 extend along at least 70% of the side edges of the front portion 4.

The side panels 7, 8 are elastic and are preferably made from elastic material apart from the parts which comprise the fastening elements 10, which parts can consist of inelastic material. The elastic material can consist of elastomers made from block copolymers, such as polyurethanes, copolyether esters, polyamide-polyether block copolymers, ethylene-vinylacetates (EVAs) and the like, including polyurethanes available from E.I Du Pont de Nemours Co., USA under the name LYCRA® (also known as spandex); elastomeric styrene-butadiene copolymers, including those such as KRATON® material, which are available from Shell Chemical Company of Houston, Tex., USA; tetrablock copolymers, including elastomeric styrene-poly(ethylene-propylene) block copolymers available from Shell Chemical Company of Houston, Tex., USA under the trade name KRATON®; polyamides including polyether block amides available from Ato Chemical Company, USA under the trade name PEBAX®; polyesters, such as those available from E.I Du Pont de Nemours Co. under the trade name HYTREL®; single-site or metallocene-catalyzed polymers, including single-site or metallocene-catalyzed polyolefins with a density of less than around 0.89 g/cm$^3$ from Dow Chemical Co., USA under the trade name AFFINITY®; and natural and synthetic rubber.

The purpose of the elastic side panels is to give the pant diaper a good fit. The side panels are dimensioned so as to provide the necessary elastic force but no more. It is therefore conceivable for the side panels also to have parts made of inelastic material in places other than at the fastening elements. Such an inelastic material can consist of a non-woven material, for example a spunbond non-woven, a carded non-woven, a meltblown non-woven or a non-woven laminate, for example a spunbond-meltblown-spunbond (SMS) laminate. The fibres used for constructing the non-woven materials can consist of fibres made of polyolefins, for example polyethylene or polypropylene, or of polyester. The non-woven material can also consist of a mixture of a number of different types of fibre or of fibres which consist of a number of different polymers, what are known as copolymers. It is also possible for the inelastic material to consist of a plastic film.

It is also conceivable to make use of, for example, two non-woven layers, between which elastic materials, elastic bands or elastic threads in a stretched state are attached, as the material for the side panels. In such a material, the elastic and inelastic parts of the side panels consist of portions with and without such elastic materials.

As can be seen from FIG. 1, the diaper also comprises leg elastic 12 which consists of the lower portion of the side panels 7, 8 and one or more elastic threads which are arranged between the surface layers 2 and 3 and are attached to these in a stretched state on both sides of the absorption body 1. Elastic bands 13, 14, which are attached to both surface layers 2, 3 in a stretched state, also form waist elastic in the front and rear portions of the diaper.

The liquid-permeable surface layer 2 consists of, for example, a non-woven made of spunbond polypropylene. Other materials which are used for liquid-permeable surface layers, what are known as top sheets, for absorbent articles, such as non-wovens made of synthetic and/or natural fibres, perforated plastic films or laminates of such materials, can of course also be used as the surface layer 2.

The liquidtight outer surface layer 3 can consist of a plastic layer, preferably of a breathable type, or a laminate consisting of a plastic layer and a non-woven. All materials which are used as what are known as backing layers for absorbent articles can be used.

The absorption body 1 preferably comprises a layer of cellulose fibres with or without superabsorbents and/or binding fibres mixed in. Other materials, such as foamed materials or moss, can also be used. The absorption body can also be constructed from a number of layers and advantageously comprises a layer of a material with high permeability, for example a wadding layer.

The fastening elements 11 are preferably trapezoid with parallel short sides 11A, 11B, a short long side 11C, which extends at right angles to the short sides, and a long side 11D, which is inclined relative to the short long side 11C. The fastening elements 11 are attached to the outside of the surface layer 2 in the side edge portions of the front portion 4 with the long sides facing one another and with the long short sides positioned next to the waist edge of the diaper. The fastening element 10 which interacts with the fastening elements 11 preferably has a rectangular shape and a width which is the same as or smaller than the width of the shortest short side of the fastening elements 11. In the longitudinal direction of the diaper, the fastening elements 10, 11 extend along the entire side edge of the front portion.

Figure 7:
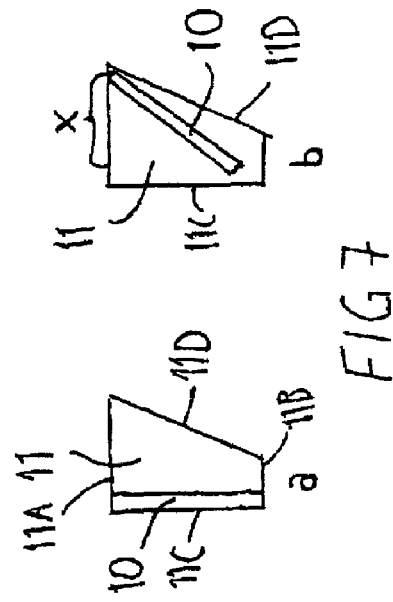
FIGS. 7a and 7b show diagrammatically a fastening means according to an embodiment of the invention with the male element placed in different positions.

FIGS. 7a and 7b show the male element 10 in its two extreme positions on the female element 11. In the position shown in FIG. 7a, in which the element 10 extends along the short long side 11C of the element 11, the waist size of the diaper is at its maximum whereas, in the position shown in FIG. 7b, it is at its minimum. In FIG. 7b, the fastening element 10 has been rotated so that its edge lying next to the waistband is located at as great a distance as possible from the short long side 11C of the element 11. In this way, the waist size is reduced by the length x in FIG. 7b, that is to say, if the fastening elements 10 of both fastening means 9 are positioned in a manner corresponding to FIG. 7b, the waist size is reduced by 2x.

By virtue of the fact that the short side 11B of the fastening element 11 is longer than the width of the fastening element 10, a small adjustment possibility for reducing the size of the leg opening 12 is also obtained.

By utilizing trapezoid fastening elements of the female type, the quantity of fastening element material for bringing about a certain adjustment length of the waist size can be substantially reduced in a simple manner, which means a considerable cost saving. Furthermore, such material is present in only the places where it is required, which means that its influence on the product in terms of, for example, increased local rigidity and reduced local flexibility is reduced.

In the embodiment described, the fastening means consist of interacting mechanical fastening elements, but it is also conceivable to use adhesive male elements which interact with female elements made of material which allows unfastening of the adhesive without the material being damaged or the adhesive force being reduced appreciably.

An embodiment of a method for manufacturing diapers according to FIG. 1 will now be described with reference to FIGS. 2 and 3. In order to simplify comparison with the diaper in FIG. 1, components in FIGS. 2 and 3 have been given the same reference numbers as corresponding components of the finished diaper in FIG. 1. For example, the web of liquid-permeable material in FIGS. 2 and 3 has been given the same reference number as the surface layer 2 of the finished diaper.

A diaper according to FIG. 1 is manufactured in the manner described below.

Absorption bodies 1 are applied to a moving material web 2 of liquid-permeable material by means of, for example, a transfer wheel, onto which absorption bodies 1 formed in a mat-forming wheel have been distributed. The feed direction of the material web 2 is indicated by an arrow in FIG. 2. If the forming of absorption bodies 1 can take place synchronously with the advance of the material web 2, the transfer wheel can be omitted, and the wheel can consist of a mat-forming wheel. The moulds of the mat-forming wheel are suitably designed so that the absorption bodies which leave the mat-forming wheel have front ends and rear ends facing one another. If this is not the case, the transfer from the mat-forming wheel is effected in such a manner that every other absorption body is rotated by 180° before the absorption bodies are distributed onto the transfer wheel. The absorption bodies 1 are therefore distributed onto the material web 2 in a row with front portions and rear portions of adjacent absorption bodies facing one another. The material web 2 and components added to it subsequently therefore constitute a web of consecutive diaper blanks in different manufacturing stages.

Elastic threads are then applied along the edges of the future leg openings 12, and elastic bands 13, 14 are applied in the interspaces between the absorption bodies 1 in the row of laid-out absorption bodies.

A material web 3 of liquidtight material is then applied on top of the row of absorption bodies 1. Directly before application, the material web 3 passes through a gluing unit and is attached, by means of a roller pair, to the material web 2 in parts lying outside the absorption bodies 1. The material web 3 may also be attached to the rear side of every absorption body 1. The manufacturing steps described so far are conventional and well-known to the person skilled in the art.

Trapezoid fastening elements 15A-15D are then applied to the liquidtight surface layer 3 in the front portions 4 in a manner which will be described in greater detail below with reference to FIG. 3. The material pieces 16, 17 are then attached to the side edges of the rear portions 5, after which individual diapers with side panels 16A, 17A and, respectively, 16B, 17B and leg openings are cut out of the web of consecutive diaper blanks. In the figure, this cutting-out is indicated by a scissors symbol. After having been formed into finished diapers, the diapers are conveyed to a packing station.

Strips of fastening element material of the male type, that is to say comprising hook means, are attached to the side panel blanks 16, 17 either before or after these are attached to the web of consecutive diaper blanks. The fastening element strips are preferably applied to the side panel blanks 16, 17 in advance before these are attached to the web of consecutive diaper blanks.

FIG. 3 shows on larger scale than in FIG. 2 how a sequence of fastening elements 15A-15D is cut out of a web 15 of fastening element material and applied to a web of diaper blanks. The feed directions of the two webs are indicated by arrows in FIG. 3. The embodiment shown in FIG. 3 differs from that shown in FIG. 2 only in that the web 15 runs to the left of the diaper blank web in FIG. 3 and the leg openings in the diaper blank web in FIG. 3 are already cut out. However, these differences have no significance for the method of cutting-out and applying fastening elements illustrated in FIGS. 2 and 3.

In order to produce the elements 15A-15D, the web 15 is cut alternately with cuts S1, S3, which extend entirely in the transverse direction of the web at right angles to the feed direction, and with cuts S2, S4, which extend in an inclined manner in relation to the transverse direction and the feed direction. The inclined cuts S2, S4 are inclined in different directions but at the same angle to the transverse direction. In this way, sequences of four trapezoid fastening elements 15A-15D are produced, in which the first element 15A and fourth element 15D on the one hand and the second element 15B and third element 15C on the other hand have their long short sides along the same side edge of the web 15. In this text, short sides mean those sides of the parallel trapezia which are parallel to one another even if these sides should be longer than one or both of the long sides.

The cut-out fastening elements are then transferred in a suitable manner to the diaper blank web and are positioned in the intended places in the two opposite front portions 4 of the diaper blanks in the diaper blank web. The transfer can take place by means of four arms, each having gripping means, for example suction means, for taking hold of a fastening element, which move the elements 15A-15D to the intended places. This movement preferably takes place synchronously with the feed of the diaper blank web so that the elements 15A-15D only have to be moved in the lateral direction and the vertical direction. In such an embodiment, which is illustrated diagrammatically in FIG. 2, first the second and third elements 15B and 15C are moved laterally and then pressed firmly against the diaper blank web, after which the first and fourth elements 15A and 15D are moved -laterally. The attachment of the elements 15A-15D can take place by means of thermal or ultrasonic welding or by means of gluing. In the event of gluing, the elements 15A-15D suitably pass through a gluing unit during their movement to the diaper blank web. It is of course also possible to carry out the movement of the elements 15A-15D simultaneously for all the elements or separately, that is to say each element is moved directly after cutting-out, and with a movement component in the feed direction of the diaper web.

For reasons of clarity, the cutting-out of the elements 15A-15D is shown as taking place in the lateral direction outside the diaper blank web but, if space allows, it is also possible for cutting-out to take place above the diaper blank web in order to reduce the length of the necessary lateral movements of the fastening elements.

Figure 4:
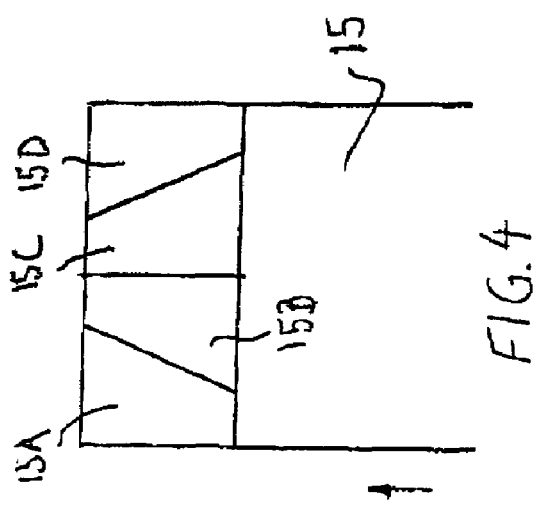
FIG. 4 shows an alternative design of the fastening element material web and the cutting-out of individual elements therefrom.

In the embodiment shown in FIG. 3, the cutting-out of fastening elements takes place from a material web which has a width which is the same as the height of the fastening elements, that is to say the length of the long side which is to extend along the side edges of the front portion of the diaper. FIG. 4 shows an embodiment where the cutting-out of the elements 15A-15D takes place from a material web which has a width which is the same as the length of a sequence of cut-out elements 15A-15D. In such a web, transverse cuts are made at a distance from one another which corresponds to the height of the fastening elements, after which one entirely longitudinally directed cut and two longitudinal cuts inclined towards one another are made. It is of course possible to make the longitudinal cuts before the transverse cut if so desired. Otherwise, neither the cutting-out nor the application differ from what was described with reference to FIGS. 2 and 3.

FIG. 5 shows diagrammatically a fastening element web 15 which has been provided with a series of successively arranged strips of male element material, each strip having double the width of a male element 10, located at a distance from one another which corresponds to the combined length of the short sides of a trapeziform element 15A-15D. Furthermore, the tops of some of the hook means of the male elements are firmly connected to the female element web, for example by thermal or ultrasonic welding or by gluing. It can be seen that fastening elements of the female type provided with male elements 10 in accordance with what is shown in FIG. 5 can also be manufactured in a fastening element web according to FIG. 4 simply by arranging male element strips along the longitudinal edges of such a web and along its center line.

A design according to FIG. 5 is suitable if a pant diaper with childproof unfastenable and reclosable fastening means for interconnection of the side edges of the front and rear portions is to be manufactured. A childproof connection that is difficult or impossible for an infant to open but easy for an adult to open is obtained. It has of course been found that infants like to tamper with their pant diapers and that there is therefore a need for a childproof connection. The number of firmly connected points should be selected so that the force which is required to open such a connection is greater than 4 N, preferably greater than 6 N, more preferably greater than 8 N and most preferably greater than 10 N but smaller than 20 and preferably smaller than 15 N in order to ensure childproofness and make the connection easy to open for an adult. The opening force can be measured simply in the manner shown diagrammatically in FIG. 7 by connecting a weight to that part of the two parts of the connection which is overlapped, and then taking hold of the grip part of the overlapping part and lifting the connection. If the weight remains hanging from the connection for more than 30 seconds without the connection coming undone, the connection is considered to hold for the weight concerned.

Figure 6:
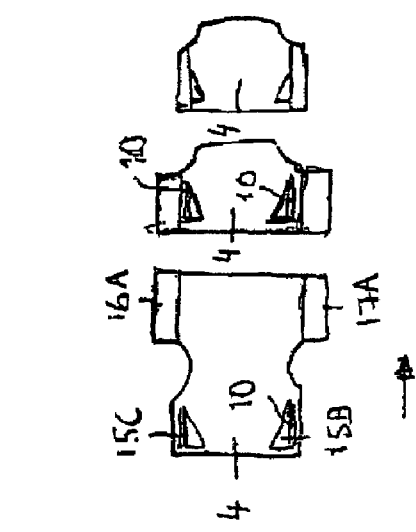
FIG. 6 shows diagrammatically the final steps in the manufacture of a pant diaper.
Figure 8:
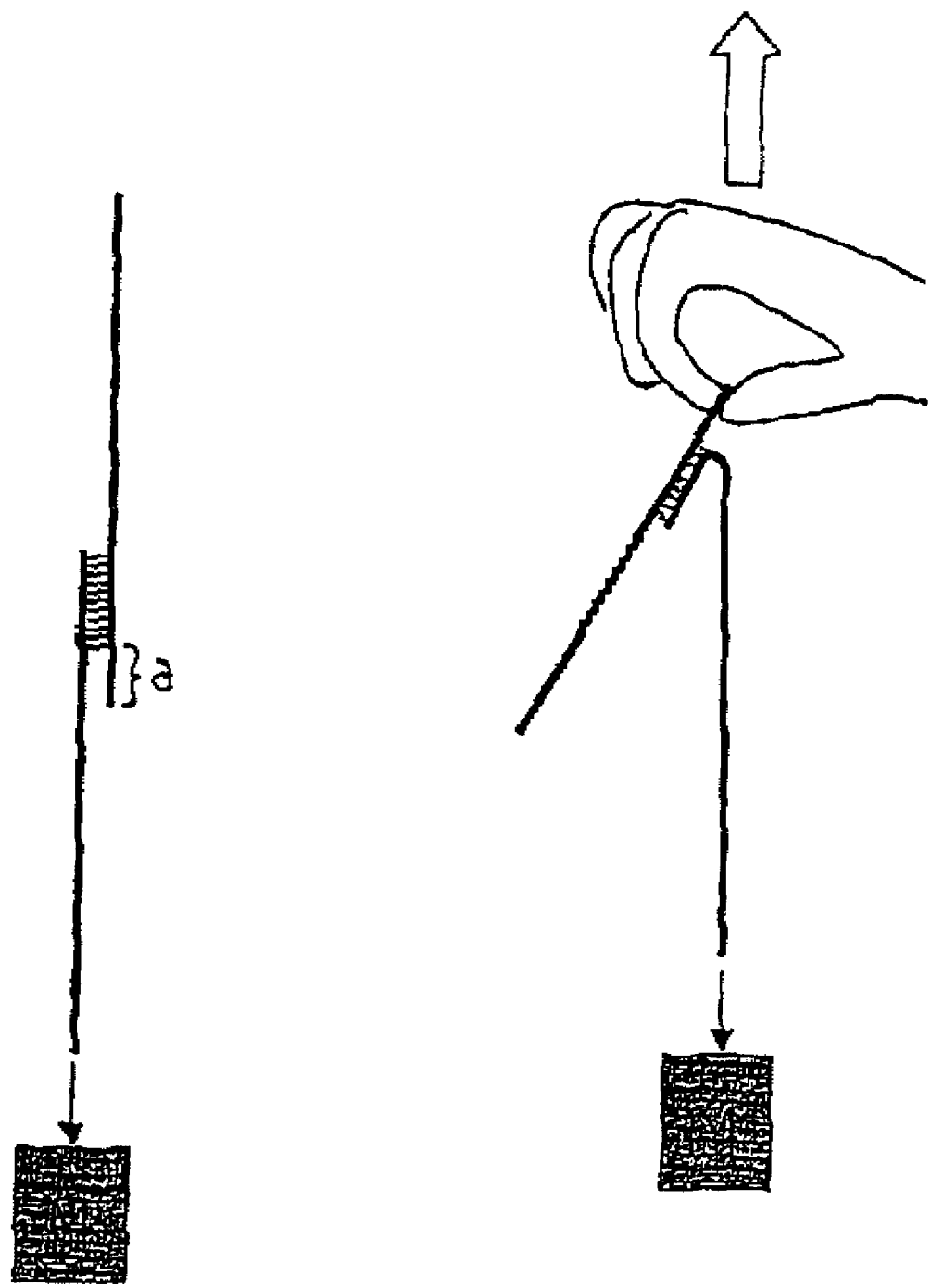
FIG. 8 shows a method of testing the childproofness of a connection.

The blanks for pant diapers according to the invention can suitably be manufactured in the same way as described with reference to FIGS. 2-5. FIG. 6 illustrates the final steps of such manufacture and FIG. 6 can be considered to constitute a supplement to FIG. 2, that is to say FIG. 6 begins where FIG. 2 ends, namely with the cutting-out of diapers. The pant diaper blank shown in FIG. 6 corresponds to a diaper produced according to FIG. 2 with the modification that it is provided with fastening elements in accordance with FIG. 5, that is to say the fastening elements 10 are already fastened to the female elements 15 when these are cut out. In order to produce a pant diaper from the blank shown in FIG. 6, the pant diaper blank is folded around a transverse axis so that the front and rear portions come to lie edge to edge. The side panels 16, 17 are then folded in over the side edges of the front portion 4, and the folded-in parts of the side panels 16, 17 are finally attached in a suitable manner to the fastening elements 10, for example by gluing or thermal or ultrasonic welding.

In the embodiment described, the web 3 of liquidtight material is laid on top of the web 2 of liquid-permeable material after absorption bodies have been distributed onto the latter. It is of course possible for the webs to be the other way round, so that absorption bodies are distributed onto the web of liquidtight material and the web of liquid-permeable material is applied last. In such an application, the fastening elements can be attached to the web 3 before absorption bodies are applied to the latter.

It is of course also conceivable for the fastening elements to be the other way round in such a manner that the rectangular and elongate male elements are attached to the outside of the front portion and the parallel-trapeziform female elements are attached to the inside of the rear portion, in which case adjustment is brought about by the female elements being placed in different positions on the male elements. However, this is not preferred. It is also conceivable to place the female elements on the outside of the rear portion and the male elements on the inside of the front portion.

The method described can of course be modified within the scope of the invention. For example, the side panels 16, 17 can be applied to the material web 2 before the material web 3 is applied, so that the side panels are arranged between the material webs 2 and 3 and are attached to both these webs. The side panels can also be attached to the liquid-permeable surface layer. The absorption bodies 1 can be supplemented by further layers by such layers being applied on top of the bodies 1 by additional transfer or mat-forming wheels being added to the process line shown in FIG. 2. Means for providing liquid barriers, what are known as standing gathers, can also be added to the process line. The leg elastic and the waist elastic, which preferably extend along the front and rear edges of the pant diaper, do not have to be arranged between the material webs 2 and 3 but can be applied to one of these webs. The absorption bodies can have a shape different to that shown, for example rectangular or hourglass-shaped. Types of mechanical fastening element other than hook and loop means can be used, for example various types of snap connections, which can also be childproofed. The components included in the process line described are of such a type as is normally used in manufacturing diapers, pant diapers and similar articles and can be replaced by other components with the same function. The invention is therefore to be limited only by the content of the accompanying patent claims.

The invention is not limited to the illustrative embodiments described above, but a number of modifications are possible within the scope of the patent claims below.

What is claimed is:

1. An absorbent article, comprising an absorption body enclosed between an inner liquid-permeable surface layer and an outer liquidtight surface layer and also a front portion, a rear portion and a crotch portion which lies between the front and rear portions and includes and is delimited by the leg openings of the article, the front and rear portions each have a first edge defining a waist edge of the absorbent article and two side edges that each extend between the waist edge and a leg opening, the absorbent article further comprising fasteners for openably and reclosably fastening mutually opposite side parts of the front portion and the rear portion to one another, which fasteners comprise interacting pairs of fastening elements, which extend along the side edges of the front and rear portions, wherein one of the elements of each of the pairs of fastening elements is a tapering element, wherein the tapering element has a tapering edge that is not adjacent to the particular side edge of the front or rear portion that the tapering element is closest to, wherein the tapering edge tapers continuously from a first edge of the tapering element closest to the first edge of the front portion or rear portion towards a second edge of the tapering element closest to the leg opening, such that the tapering element is widest in the transverse direction at the first edge thereof that is closest to the waist edge and is narrowest in the transverse direction towards the leg opening, wherein the one fastening element of each pair with tapering is a separate fastening material applied to the absorbent article, wherein the fastening elements are components which are adapted to actively engage in attachment to another fastening element.

2. The article according to claim 1, wherein the tapering fastening elements are trapezoid with two parallel short sides, a short long side, which extends at right angles to the short sides, and a long side, which is located at a greater distance from the closest side edge of that portion of the article to which the element is attached than the short long side.

3. The article according to claim 2, wherein the fastening element which interacts with the tapering fastening element is elongate and rectangular, in that the width of the shortest short side of the tapering fastening element is the same as or greater than the width of the elongate fastening element, and in that the length of the elongate fastening element and the length of the shortest long side of the tapering fastening element lie between 70-100% of the length of the side edges of the front portion.

4. The article according to claim 1, wherein each element of the each pair of fastening elements is tapered.

5. The article according to claim 4, wherein each element of the each pair of fastening elements has the same size.

6. An absorbent article, comprising an absorption body enclosed between an inner liquid-permeable surface layer and an outer liquidtight surface layer and also a front portion, a rear portion and a crotch portion which lies between the front and rear portions and includes and is delimited by the leg openings of the article, the front and rear portions each have a first edge defining a waist edge of the absorbent article and two side edges that each extend between the waist edge and a leg opening, the absorbent article further comprising fasteners for openably and reclosably fastening mutually opposite side parts of the front portion and the rear portion to one another, which fasteners comprise interacting pairs of fastening elements, which extend along the side edges of the front and rear portions, wherein one of the elements of each of the pairs of fastening elements is a tapering element, wherein the tapering element has a tapering edge that is not adjacent to the particular side edge of the front or rear portion that the tapering element is closest to, wherein the tapering edge tapers continuously from a first edge of the tapering element closest to the first edge of the front portion or rear portion towards a second edge of the tapering element closest to the leg opening, such that the tapering element is widest in the transverse direction at the first edge thereof that is closest to the waist edge and is narrowest in the transverse direction towards the leg opening, wherein the one fastening element of each pair with tapering is a separate fastening material applied to the absorbent article, wherein the fastening elements are adapted to allow adjustment of the length of the waist edge or the size of leg openings, which leg openings are formed from the absorbent article being in a fastened state, wherein the fastening elements are components which are adapted to actively engage in attachment to another fastening element.

7. The article according to claim 6, wherein the tapering fastening elements are trapezoid with two parallel short sides, a short long side, which extends at right angles to the short sides, and a long side, which is located at a greater distance from the closest side edge of that portion of the article to which the element is attached than the short long side.

8. The article according to claim 7, wherein the fastening element which interacts with the tapering fastening element is elongate and rectangular, in that the width of the shortest short side of the tapering fastening element is the same as or greater than the width of the elongate fastening element, and in that the length of the elongate fastening element and the length of the shortest long side of the tapering fastening element lie between 70-100% of the length of the side edges of the front portion.

9. An absorbent article, comprising an absorption body enclosed between an inner liquid-permeable surface layer and an outer liquidtight surface layer and also a front portion, a rear portion and a crotch portion which lies between the front and rear portions and includes and is delimited by the leg openings of the article, the front and rear portions each have a first edge defining a waist edge of the absorbent article and two side edges that each extend between the waist edge and a leg opening, the absorbent article further comprising fasteners for openably and reclosably fastening mutually opposite side parts of the front portion and the rear portion to one another, which fasteners comprise interacting pairs of fastening elements, which extend along the side edges of the front and rear portions, wherein one of the elements of each of the pairs of fastening elements is a tapering element, wherein the tapering element has a tapering edge that is not adjacent to the particular side edge of the front or rear portion that the tapering element is closest to, wherein the tapering edge tapers continuously from a first edge of the tapering element closest to the first edge of the front portion or rear portion towards a second edge of the tapering element closest to the leg opening, such that the tapering element is widest in the transverse direction at the first edge thereof that is closest to the waist edge and is narrowest in the transverse direction towards the leg opening, wherein the one fastening element of each pair with tapering is a separate fastening material applied to the absorbent article, wherein the fastening elements are adapted to allow adjustment of the length of the waist edge and the size of leg openings, which leg openings are formed from the absorbent article being in a fastened state, wherein the fastening elements are components which are adapted to actively engage in attachment to another fastening element.

10. The article according to claim 9, wherein the tapering fastening elements are trapezoid with two parallel short sides, a short long side, which extends at right angles to the short sides, and a long side, which is located at a greater distance from the closest side edge of that portion of the article to which the element is attached than the short long side.

11. The article according to claim 10, wherein the fastening element which interacts with the tapering fastening element is elongate and rectangular, in that the width of the shortest short side of the tapering fastening element is the same as or greater than the width of the elongate fastening element, and in that the length of the elongate fastening element and the length of the shortest long side of the tapering fastening element lie between 70-100% of the length of the side edges of the front portion.

* * * * *